(12) United States Patent
Hawkins et al.

(10) Patent No.: US 9,011,828 B2
(45) Date of Patent: Apr. 21, 2015

(54) COMPOSITIONS AND METHODS FOR PERMANENT STRAIGHTENING OF HAIR

(75) Inventors: Geoffrey Hawkins, Yardley, PA (US); Jean Harry Xavier, Holbrook, NY (US); Lavinia C. Popescu, Jackson Heights, NY (US); Jennifer Marie Recine, Seaford, NY (US); Christina Lynn Marrone, Selden, NY (US)

(73) Assignee: ELC Management, LLC

( * ) Notice: Subject to any disclaimer, the term of this patent is extended or adjusted under 35 U.S.C. 154(b) by 249 days.

(21) Appl. No.: 13/074,247

(22) Filed: Mar. 29, 2011

(65) Prior Publication Data
US 2012/0186597 A1    Jul. 26, 2012

Related U.S. Application Data

(63) Continuation-in-part of application No. 13/013,482, filed on Jan. 25, 2011, now abandoned.

(51) Int. Cl.
| | | |
|---|---|---|
| *A61Q 5/04* | (2006.01) |
| *A45D 7/00* | (2006.01) |
| *A45D 7/06* | (2006.01) |
| *A61K 8/66* | (2006.01) |
| *A61K 8/23* | (2006.01) |

(52) U.S. Cl.
CPC .. *A45D 7/00* (2013.01); *A45D 7/06* (2013.01); *A61Q 5/04* (2013.01); *A61K 8/66* (2013.01); *A61K 8/23* (2013.01)

(58) Field of Classification Search
None
See application file for complete search history.

(56) References Cited

U.S. PATENT DOCUMENTS

| | | | |
|---|---|---|---|
| 4,424,820 A * | 1/1984 | Cannell et al. | 132/204 |
| 4,895,722 A | 1/1990 | Abe et al. | |
| 5,395,490 A | 3/1995 | Hoff et al. | |
| 5,490,980 A | 2/1996 | Richardson et al. | |
| 5,525,336 A | 6/1996 | Green et al. | |
| 5,562,110 A | 10/1996 | Ottenbrite et al. | |
| 8,025,703 B2 * | 9/2011 | Ogawa et al. | 8/405 |
| 2002/0197224 A1 * | 12/2002 | Slusarewicz | 424/70.6 |
| 2005/0208004 A1 * | 9/2005 | Romero et al. | 424/70.1 |
| 2006/0115445 A1 | 6/2006 | Brun et al. | |
| 2008/0213206 A1 | 9/2008 | Philippe et al. | |
| 2009/0071495 A1 * | 3/2009 | Nguyen et al. | 132/203 |
| 2009/0126754 A1 | 5/2009 | Popescu et al. | |

FOREIGN PATENT DOCUMENTS

| | | |
|---|---|---|
| JP | 3083908 | 4/1991 |
| JP | 2719166 | 2/1998 |
| WO | 0121139 | 3/2001 |
| WO | 0121145 | 3/2001 |
| WO | 2010096598 | 8/2010 |
| WO | 2010096598 A2 | 8/2010 |
| WO | 2010096605 | 8/2010 |
| WO | 2010096610 | 8/2010 |

OTHER PUBLICATIONS

Paguirigan, et al.; Nature Protocols; Protocol for the fabrication of enzymatically crosslinked gelatin microchannels for microfluidic cell culture; vol. 2; No. 7; pp. 1782-1788; 2007.
Yokoyama, et al.; Appl. Microbiol Biotechnol; Properties and applications of microbial transglutaminase; 64(4); pp. 447-454; 2004. (Eng. Abstract).
PCT International Search Report International Application No. PCT/US2011/063659; Mailing Date: Jul. 20, 2012; Date of Completion: Jul. 20, 2012.
PCT Written Opinion of the International Searching Authority; International Application No. PCT/US2011/063659; Mailing Date: Jul. 20, 2012; Completion Date: Jul. 20, 2012.

* cited by examiner

*Primary Examiner* — Jyothsna Venkat
(74) *Attorney, Agent, or Firm* — Peter Giancana

(57) ABSTRACT

Improved hair straightening topical compositions comprising transglutaminase, sodium metabisulfite, and a system for stabilizing the pH of the composition, and for inhibiting the generation of sulfur dioxide. Optionally, one or more additional hair straightening agents, that are capable of affecting secondary, tertiary and quaternary protein structures of human hair may be included. Optionally, polylysine may be included which, in combination with TGase, acts to form a surface barrier film and moisture shield around human hair. The invention includes methods of using such topical compositions.

11 Claims, No Drawings

COMPOSITIONS AND METHODS FOR PERMANENT STRAIGHTENING OF HAIR

The present application is a continuation-in-part of application U.S. Ser. No. 13/013,482, filed Jan. 25, 2011 now abandoned.

FIELD OF THE INVENTION

The invention is in the field of hair straightening. More particularly, it is in the field of improved compositions and methods for permanent straightening of human hair.

BACKGROUND OF THE INVENTION

Various methods of straightening hair are known, each having it's own advantages and disadvantages to a more or lesser degree. Hair straightening technologies include those that alter the primary protein structure of hair, those that alter secondary or tertiary protein structure, and those that hold hair in a straightened configuration against the hair's natural tendency to curl.

In parent application U.S. Ser. No. 13/013,482 (herein incorporated by reference, in its entirety), we disclosed new and useful hair straightening compositions comprising polylysine and transglutaminase, preferably also sodium metabisulfite, $Na_2S_2O_5$, and optionally tourmaline and calcium; in a cosmetically acceptable base maintained at a pH of 5.0 to 7.5. The efficacy of the composition was dependent on the pH. However, although such products are effective hair strengtheners, over time we have noticed that efficacy diminished. In the present invention, our solution to this problem results in new and improved hair straightening compositions.

Human Hair

U.S. Pat. No. 5,395,490 is herein incorporated by reference, in its entirety. Several figures in U.S. Pat. No. 5,395,490 diagram the structure of human hair fibers, the protein components of hair, and energy levels of the disulfide bond. A fiber of human hair comprises three main morphological components: the cuticle, the cortex, and the cell membrane complex, which itself is comprised of a protein matrix of keratin peptide chains.

The natural shape and structural integrity of human hair depends, in part, on the orientation of disulfide bonds (cysteine-cysteine bonds). In human hair, disulfide bonds that link one part of a peptide chain with another part of the same chain contribute to tertiary protein structure, while disulfide bonds that link two different peptide chains contribute to quaternary structure. Furthermore, disulfide bonds are known to protect secondary protein structures in the immediate vicinity of the bond. They may do this by shielding hydrogen bonds.

Thus, it is generally thought that alteration of the disulfide bonds is necessary and/or useful to effect long term changes in the shape of hair. Hair shaping treatments that do not rearrange the disulfide bonds result in changes in hair shape that last a relatively short time. For example, the use of heat to style hair may create temporary straightening of the hair. However, the styled hair will return to its natural shape after a short time, as a result of exposure to moisture in the air or washing. The use of heat and moisture to straighten hair may break and reconfigure hydrogen bonds in the hair, but the disulfide bonds are not substantially affected. It is thought that hydrogen bonds, by themselves, are insufficient to hold the shape of hair for a significant time, because the stronger disulfide bonds eventually force the hair to reassume its original shape. Thus, a permanent straightening of the hair is thought to involve the cleaving and reforming of a substantial number of disulfide bonds. Various chemical treatments for doing this are known.

Chemical Hair Straightening Treatments

Hair straightening by treating the hair with chemical agents is well known. Depending on the straightening agent used, damage to the protein structure may be controlled to a more or less degree. That is, various types of protein structures of the treated hair may be broken down, or only a select type of protein structure. For example, hair straightening products that alter primary structure, do so by weakening and/or breaking the internal chemical bonds of hair protein amino acids. Regardless of where the protein structure is altered, effective straightening treatments cause natural curls to loosen and straighten. While some straightening agents may be more effective and/or efficient than others, the trade off is usually in the damage done to the hair and scalp, and the need for adjunct treatments to limit that damage. On the other hand, treatments which may be somewhat less damaging to the hair and scalp, may require a longer time to operate, or the application of significantly more product, or multiple applications to achieve a desired result.

Among known hair straightening products that alter primary structure we may name products comprising sodium hydroxide, potassium hydroxide, lithium hydroxide, and guanidine hydroxide. It is generally acknowledged that repeated use of hydroxide hair straightening products can be very damaging to hair.

Among hair straightening products that disrupt tertiary, and perhaps quaternary structure, we can name ammonium thioglycolate, ammonium sulfite, ammonium bisulfite, sodium metabisulfite ($Na_2S_2O_5$), and cysteine. These sulfur-containing agents are more targeted in the damage that they inflict on hair proteins. These agents act primarily by selectively weakening or cleaving the disulfide bonds in cystine, instead of disrupting the entire protein. First, the sulfur-containing agent is used to reduce disulfide bonds, along with the application of mechanical stress. Next, new disulfide bonds are allowed to form, in a new arrangement, thus giving the hair a new shape. An oxidizing agent may be used to help constitute the new disulfide bonds. In the art of hair straightening, repeated use of ammonium thioglycolate or cysteine is considered significantly damaging to hair, while ammonium sulfite and ammonium bisulfite also cause damage.

Hair straightening products based on formaldehyde are also known, and have come under some scrutiny by health authorities in recent months. In general, known chemical treatments are considered harsh and damaging to human hair and skin. The damage done to hair is measured as a loss of cystine content (fewer S—S bonds indicating a loss of protein structure), a decrease in water contact angle (loss of hydrophobicity), an increase in microscopic damage to cuticle (swelling and lifting), a decrease in mechanical break strength. Some visible manifestations of the negative effects of chemical hair styling include dry, brittle or limp hair, and a loss of shine and/or color.

In addition to the damage that various salon and retail hair treatments may cause to hair, the risk posed to a user's health is also a concern. Any health risks that may exist pertain to the person whose hair is being treated, but more especially they pertain to hair styling professionals who experience repeated or persistent exposure to hair treatment chemicals and/or to chemicals that are generated in the process of treating the hair. In general, a retail consumer or a salon professional may come into physical contact with hair treatment chemicals and/or be exposed to vapors given off by hair treatment products. Skin irritation, allergic reaction and headaches are some of the symptoms of excessive exposure to one or more chemicals that may be found in commercially available and professionally available products. A product that does not elicit an adverse reaction, even after extended exposure, is certainly preferred over less benign products.

Transglutaminase

Transglutaminases are a family of enzymes with the ability to covalently bond protein bound glutamine and protein bound lysine. Transglutaminases (hereinafter, TGase) catalyze the posttranslational modification of proteins by transamidation of available glutamine residues. A major result of this activity is glutamyl-lysine cross-links in proteins. Glutamine is readily available in hair, while lysine is present to lesser degree. Some TGases are found naturally throughout the body, including the hair. Other TGases are present in animal, plant and microbial sources. Available sources of transglutaminase include, but are not limited to, slime mold, alfalfa, guinea pig, and bacteria. Used topically, TGase may contribute to the overall protein structure of hair.

Commonly owned, co-pending application, US2009-0126754, discloses the use of topically applied transglutaminase (without any free lysine) to retain curl in curled hair. However, it was also reported that when a commercially available transglutaminase blend was present at concentrations of 2%, 5% and 10%, the product caused curled hair to droop, within 30 minutes of application, by as much 25%, 33% and 16% respectively. Despite this, curl was not eliminated completely, and the hair was not straightened to a sufficient degree to consider these products as commercially viable hair straightening products, based on TGase alone.

A number of other topical uses for transglutaminases have been proposed. JP 2719166 discloses compositions containing transglutaminase and a polyhydric alcohol, said to be useful in treatment of damaged hair by increasing the moisture retention of the hair. JP 3-083908 suggests the use of transglutaminase in combination with polyethylene glycol or other water soluble materials to treat chapped skin. It has also been suggested for use in binding active components to skin, hair or nails (U.S. Pat. No. 5,490,980). WO01/21145 teaches the use of transglutaminase to improve the color-fastness of hair dyes. WO01/21139 suggests a combination of transglutaminase and an active substance having substrate activity for transglutaminase, for use in restructuring damaged keratin fibers. U.S. Pat. No. 5,525,336 discloses the combination of corneocyte proteins and transglutaminase for application to skin, hair or nails to form a protective layer.

Tourmaline

Hair straightening products that alter secondary or tertiary structure include those that comprise tourmaline. Tourmaline is an acentric rhombohedral borosilicate characterized by six-membered tetrahedral rings. It is a semi-precious stone, and a crystal silicate compounded with varying amount of elements such as aluminum, iron, magnesium, sodium, lithium, or potassium. The beneficial effects and advantages of heat activated tourmaline on hair proteins has been discussed at length in commonly owned applications WO2010/096598, WO2010/096605, and WO2010/096610, herein incorporated by reference, in their entirety.

SUMMARY OF THE INVENTION

The present invention encompasses improved hair straightening topical compositions comprising transglutaminase, sodium metabisulfite, and a system for stabilizing the pH of the composition and for inhibiting the generation of sulfur dioxide.

Optionally, one or more additional hair straightening agents, that are capable of affecting secondary, tertiary and quaternary protein structures of human hair may be included; for example, tourmaline. Optionally, polylysine may be included which, in combination with TGase, acts to form a surface barrier film and moisture shield around human hair. The hair straightening agents effect a permanent straightening of hair through changes in the protein structure of the hair, while the surface barrier film contributes some mechanical hold, and also shields the straightened hair from ambient humidity and pollution.

The invention includes compositions that may be washed out of the hair after straightening has occurred, and compositions that are intended to remain in the hair for additional or extended benefits. The invention includes methods of using a topical composition that is capable of affecting secondary, tertiary and quaternary protein structures of human hair. Testing indicates that the hair straightening is long term and there is significantly less damage to hair compared to known heat and chemical treatments.

DETAILED DESCRIPTION OF THE INVENTION

Throughout the specification, "topical" means applied to the surface of the hair, particularly human head hair. The word "permanent" in reference to hair straightening treatments, means that the straightened shape of the hair is maintained for at least 12 washings with a shampoo containing sodium lauryl sulfate. Preferably, if the straightened hair is exposed only to once-a-day shampooing and to ambient atmospheric conditions, the straightness of the hair is maintained for at least two weeks, more preferably, at least one month, and most preferably, at least two months. Furthermore, if treated hair is saturated (i.e. during bathing), the new shape may be lost. However, "permanent" also means that once dried, the previously saturated hair will revert to its post treatment shape, to a substantial degree. Throughout the specification, "comprising" means that a collection of objects is not necessarily limited to those recited.

Transglutaminase

Some embodiments of the present invention comprises one or more transglutaminases. The transglutaminase utilized in certain embodiments of the present invention may be from various sources, including animal, plant and microbial sources. Available sources of transglutaminase include, but are not limited to, slime mold, alfalfa, guinea pig, and bacteria. In terms of weight percent, the amount of transglutaminase used in a straightening product according to the present invention may vary, and will depend on the potency of the particular enzyme utilized.

Many TGases are calcium dependent, meaning the crosslinking between glutamine and lysine requires the presence of calcium. Calcium carbonate ($CaCO_3$) is present in hair, however, when a calcium-dependent TGase is used, it is preferable if calcium is also provided in the base formula. For example, calcium in the formula may be added as $CaCO_3$. Typically, a useful amount of calcium carbonate might be about 0.05% to about 0.50%, for example 0.1% to 0.2%. Mammalian TGases tend to be calcium dependent.

Alternatively, some embodiments of the present invention utilize calcium-independent TGase, which tend to be microbial based. When using a calcium-independent TGase, it should not be necessary to add additional calcium to the base formula. One example of a calcium-independent TGase is available from Ajinomoto USA under the trade name Activa™ TG-TI. This product is a combination of maltodextrin and powdered microbial enzyme, at a nominal ration of 99:1. This microbial TGase (MTGase) is derived from a variant of *Streptomyces mobaraensis* (formerly classified as *Streptoverticillium mobaraense*). The reported activity is 81-135 U/g of Activa™ TG-TI. Other non-limiting examples of potentially useful Ajinomoto products are shown in the following table, along with several products from Yiming Biological Products Co., Ltd. (Jiangsu, China).

| | Product | Composition | Nominal Activity (U/g of product) |
|---|---|---|---|
| Ajinomoto | Activa TG-TI | 99% maltodextrin, 1.0% MTGase | 81-135 |
| | Activa TG-FP | hydrolyzed skim milk protein, MTGase | 34-65 |
| | Activa TG-GS | sodium chloride, gelatin, trisodium phosphate, maltodextrin, MTGase, safflower oil (processing aid) | 47-82 |
| | Active TG-RM | sodium caseinate, maltodextrin, MTGase | 34-65 |
| | Activa MP | maltodextrin, lactose, MTGase | 78-126 |
| Yiming Biological | TG-AD | 99.5% maltodextrin, 0.5% TGase | 40-65 |
| | TG-BH | 99% maltodextrin, 1.0% TGase | 80-130 |
| | TG-H | 90% maltodextrin, 10% TGase | 800-1300 |

In some respects, preferred transglutaminase products are those with the highest specific activity and simplest co-ingredients, as they are believed to have the best reactivity upon application and a lower potential for undesired side effects. In other respects, non-animal derived materials may be preferred, and cost is also a factor from a commercial point of view.

Polylysine

In co-pending application US2009-0126754, it was reported that concentrations of Activa™ TG-TI below 2% promote curling of hair, when topically applied. It was also reported that a commercially available TGase has a straightening effect when applied at relatively higher concentrations. However, while some straightening was observed, the hair was not straightened to a sufficient degree to make a hair straightening product based solely on TGase. Thereafter, in U.S. Ser. No. 13/013,482, we disclosed compositions having a combination of TGase and polylysine that contribute to overall hair straightening. The topical application of TGase also appears to be capable of catalyzing the covalent bonding of free polylysine supplied in a topical composition, to protein bound glutamine, near the surface of the hair.

Polylysine is a natural homopolymer of the essential amino acid L-lysine, comprising approximately 25-30 L-lysine residues. It may be produced by bacterial fermentation in the genus *Streptomyces*. In contrast to normal peptide bonds that are linked at the alpha-carbon groups, the lysine amino acids in polylysine are linked at the epsilon amino group and the carboxyl functional group. Polylysine is a cationic polymer having a positively charged hydrophilic amino group.

We observed that if sufficient TGase and sufficient polylysine were provided in a topical hair composition, the result is a continuous film on the surface of the hair. In U.S. Ser. No. 13/013,482, we demonstrated the presence of a cross-linked surface barrier film. We further demonstrated that a surface film of polylysine would act as a moisture barrier, reducing the effects of ambient humidity on treated hair. In at least two ways, this film contributes to a hair straightening composition of the present invention. First, once a polylysine film is formed on the hair via the action of TGase, the film is observed to act as a vapor and moisture barrier, that protects straightened hair from proteolytic damage, and from damage caused by environmental factors, such as ambient humidity and pollution, just to name two. Second, the continuous polylysine film, upon drying, may provide hold through the mechanical strength of the film.

We emphasize that the formation of a surface barrier film of polylysine should not be confused with the protein crosslinking that may occur between protein bound lysine and protein bound glutamine, catalyzed by TGase. To the best of our knowledge, a surface barrier film does not form from the application of TGase to the hair, in the absence of free polylysine. Nor would we expect a continuous film of this type to form on the hair from the application of TGase and non-polymerized lysine. For the surface barrier film to form, the lysine must be supplied by the topical composition, as polylysine. The moisture repelling film is covalently bonded to the hair, and does not rinse out easily, even after many washes.

This barrier film is one optional part of the hair straightening system of the present invention, and it inhibits straightened hair from returning to a curled state. Therefore, some embodiments of the present invention preferably comprise polylysine. Useful concentrations of polylysine, in commercially useful hair straightening compositions, are about 0.00001% to about 2%; preferred is about 0.1% to about 1.5%; more preferred is about 0.5% to about 1%, based on total weight of the hair straightening composition.

We also determined that the length of time required for a hair straightening effect to occur, with a composition comprising 4% Activa™ TG-TI material (activity=81-135 U/g) and 0.5% polylysine. It was determined that a straightening effect was present in all test samples, with a maximum straightening effect achieved by 30 minutes. No additional straightening was observed in samples at 45 minutes. It should be noted that the compositions of the present invention comprise additional or different hair straightening actives, and so the time required to achieve a hair straightening effect, may vary.

Concentration of TGase

The concentration of TGase used in a some embodiments of the present invention depends on the potency of the material, the intended application, and the presence of other hair straightening technologies in the composition.

As a guideline, for a hair straightening effect, each gram of hair straightening composition provides at least about 0.5 Units TGase activity, for example, at least about 1 Unit TGase activity, more preferably at least about 3 Units TGase activity, even more preferably at least about 4 Units TGase activity, and most preferably at least about 5.5 Units TGase activity per gram of composition. Beyond about 5.5 Units TGase activity per gram of hair straightening composition, little additional straightening effect due to TGase/polylysine may be observed. However, if there are no detrimental effects, larger amounts of activity can be used. With these guidelines, it is well within the skill in the art to determine the optimum concentration of any transglutaminase product of known potency.

As a specific example, let's say that the potency of Activa™ TG-TI is 100 U/g of Activa™ TG-TI. To provide 0.5 U of activity/g of composition, would require a 0.5% concentration of Activa™ TG-TI. To provide 5.5 U of activity/g of composition, would require a 5.5% concentration of Activa™ TG-TI. For the Activa™ TG-TI material specifically, in combination with polylysine, a useful concentration in a commercially useful hair straightening compositions, is about 0.5% to about 10% by weight of the total composition. A preferred concentration is between about 1.0% to about 5.0% by weight of the total composition, particularly about 2% to about 4% by weight of the total composition. About 2% of Activa™ TG-TI is most preferred, because we have noticed that a visible dust may accumulate on the hair when more is used.

Hair Reducing Agents

Embodiments of the present invention include one or more agents that are effective to reduce cystine bonds in hair, when applied topically in a composition disclosed herein. Of interest are sulfur containing agents, such as sulfites, thioglycolates, and cysteine; particularly bisulfites, more particularly, sodium metabisulfite. In compositions according to the present invention, bisulfites are especially preferred over thiols, in the sense that bisulfites provide permanent hair straightening without the use of peroxide oxidation. Preferably, compositions of the present invention comprise no sodium hydroxide, potassium hydroxide, lithium hydroxide, guanidine hydroxide, thioglycolates, cysteine, ammonium sulfite, ammonium bisulfite, or formaldehyde.

Sulfites are hair straightening agents that straighten hair by reducing disulfide bonds (S—S) to thiosulfate bonds (—S—$SO_3$), also known as a Bunte salts. Once Bunte salts are formed, the hair can be manipulated into a straightened condition. After straightening, the Bunte salts can be reoxidized without a peroxide treatment. For example, it has been reported in the literature that the formation of Bunte salts in hair treatment can be reversed with water rinsing, to rebuild the cystine bonds, but only relatively slowly. The rate of reversal may be increased by increasing the pH of the hair, for example, by washing the hair with a neutral or alkaline shampoo.

One particularly useful sulfite in the present invention is sodium metabisulfite, $Na_2S_2O_5$. As we showed in U.S. Ser. No. 13/013,482, significantly less damage was done to hair treated with compositions comprising TGase and sodium metabisulfite, compared to various commercially available products.

Thioglycolates, such as ammonium thioglycolate (a.k.a. Perm salt), and cysteine also reduce cystine bonds in hair, when applied topically, and may be used in the present invention as an adjunct reducing agent. In solution, free ammonia swells the hair, allowing thioglycolic acid to permeate the cortex and reduces the cystine bonds, forming cysteine residues. Also, the cystine bonds may be reestablished by water rinsing or hydrogen peroxide.

The one or more agents that are effective to reduce cystine bonds in hair may typically be employed in commercially useful hair straightening compositions, at concentrations of about 0.1% to about 10% of the total weight of the composition. A preferred concentration of sodium metabisulfite is about 1% to about 8%; more preferred is about 5% to about 8%, more preferred still is about 6% to about 7.75%; most preferred is at least 6.5% to a about 7.75%, by total weight of the composition.

Activated Tourmaline

The hair shaping ability of activated tourmaline has been disclosed in commonly owned applications WO2010/096598, WO2010/096605, and WO2010/096610, herein incorporated by reference, in their entirety.

Application WO2010/096598 discloses how to make a commercially acceptable personal care composition that can supply sufficient energy for reshaping human hair via disulfide bond reorganization, while remaining reasonably priced and meeting aesthetic and regulatory requirements. It was disclosed that tourmalines heated to about 70° C. or more, emit a spectrum of light having a peak wavelength around 20 μm. Furthermore, it was shown by colorimetric disulfide bond analysis that the heated (or activated) tourmaline was effective at reducing about 6-13% of S—S bonds in hair, at acidic pH, compared to control. It was also shown, that hair straightened with activated tourmaline, according to methods disclosed therein, was not weakened to a statistically significant degree. In fact, it was shown that hair treated with activated tourmaline resulted in the formation of new secondary protein structure in the treated hair. Specifically, in the tested samples, treatment with a tourmaline-containing composition, resulted in the development of strong beta structure, strong alpha+beta structure, and strong coiled-coiled structure. Thus, it was observed that a topical composition comprising activated tourmaline is able to cleave disulfide bonds, and enhance secondary structure of hair.

In WO2010/096605, it is disclosed that hair treated by an activated tourmaline composition is effective to protect hair from thermal denaturation, as well as to increase the thermal energy required to cause protein denaturation. Tourmaline seemed to cause none of the damage to hair of the type characteristic of known heat and chemical treatments.

In WO2010/096610, it is disclosed that hair treated by an activated tourmaline composition is effective to increase the level of tightly bound water in hair. Tourmaline seemed to cause none of the damage to hair of the type characteristic of known heat and chemical treatments.

In WO2010/096598, WO2010/096605, and WO2010/096610, a useful concentration of tourmaline was disclosed to be about 1% to about 10%. In the present invention, we have observed significant hair straightening effects, when tourmaline is included in a composition that comprises TGase and polylysine. Concentrations toward the lower end, i.e. about 1% to about 4% are useful to reap some or all of the benefits of tourmaline as disclosed in WO2010/096598, WO2010/096605, and WO2010/096610. Between 1% and 2% may be preferred, and about 1% may be more preferred, to avoid a whitish residue that may result from using higher concentrations.

When using heat-activated tourmaline in the present invention, it is preferable if a user applies the composition to the hair, waits a period of time during which the TGase acts, before applying heat to activate the tourmaline. This is because the heat supplied to activate the tourmaline, preferably about 70° C., is sufficient to cause break down of TGase. Therefore TGase should be allowed to work before the application of heat in excess of 30° C. Preferably, before applying heat, a user will wait about 15 to about 45 minutes. A preferred wait time is time is between 25 and 45 minutes, particularly about 30 minutes.

Compositions

In parent application U.S. Ser. No. 13/013,482, we disclosed efficacious hair straightening compositions comprising sodium metabisulfite, $Na_2S_2O_5$. As discussed therein, the optimum activity of transglutaminase is observed in a vehicle that has a pH from about 5 to about 9, for example a pH of about 5.0 to about 7.5. Based on TGase activity, a pH of about 5.5 to 7.5 is preferred, while about 6.0 to about 7.0 is more preferred. A pH of exactly 6.0 to exactly 6.5 is most preferred, in reference to TGase activity. Furthermore, sodium metabisulfite reduces cysteine. Although the reaction may take place at a pH of about 3 to about 8, it is preferred if the reaction equilibrium is shifted more toward reduction of cysteine. Therefore, as regards reduction of cysteine, a pH environment of about 5.5 to about 7.5 is preferred. For the same reason, a more preferred pH is about 5.5 to about 6.5, while about 5.8 to about 6.2 is still more preferred for the reduction of cysteine. However, it has now been observed that these compositions, while efficacious for several days after manufacture, lose a substantial amount of efficacy after one or two weeks from the date that the composition was made. Simultaneously, we observed a decrease in pH, and a release of sulfur dioxide ($SO_2$) from the composition.

After careful study, it seems that sodium metabisulfite ($Na_2S_2O_5$), which is relatively acidic, reacts with water (in the product or in the ambient atmosphere) to produce sodium bisulfite ($NaHSO_3$). Subsequently, at sufficiently low pH, sodium bisulfite is oxidized to sodium bisulfate ($NaHSO_4$). Sodium bisulfate has a fairly low acid dissociation constant ($pK_a$=1.99 in water), and dissociation leads to release of sulfur dioxide ($SO_2$). The reaction of sodium metabisulfite and sodium bisulfite are reversible and establish a dynamic equilibrium in favor of sodium bisulfite. The result is a loss of efficacy due to the loss of sodium metabisulfite, as well as the inactivation of TGase at lower pH. Also, the sulfur dioxide release is undesirable. Therefore, to have a more viable commercial product, these problems must be addressed.

These problems are addressed by including in the composition, a means of driving the dynamic equilibrium toward the formation of sodium metabisulfite, and away from the formation of sodium bisulfite. The result is a composition in which sodium metabisulfite is in dynamic equilibrium with sodium bisulfite, but the equilibrium is shifted toward the sodium metabisulfite.

Ionic Buffer System, Oxygen Scavenging System and Other Benefits

An essential component of the present invention is a system that drives the dynamic equilibrium toward the formation of sodium metabisulfite, and away from the formation of sodium bisulfite, as well as imparting other benefits, herein discussed.

One embodiment of such a system is a pH buffer/oxygen scavenging system comprising sodium sulfate ($Na_2SO_4$), and sodium sulfite ($Na_2SO_3$). These additions move the reaction equilibrium in the opposite direction, to restore/maintain levels of sodium metabisulfite, stabilize the pH of the composition, and prevent or suppress the release of $SO_2$.

Sodium Sulfite

When added to a composition according to the present invention, sodium sulfite ($Na_2SO_3$) acts as an oxygen scavenger, and thereby reduces the amount of sodium bisulfite that is oxidized, which ultimately reduces $SO_2$ generation.

Additionally, sodium sulfite acts as a reducing agent, able to form Bunte salts from S—S bonds in human hair. Therefore, compositions comprising sodium bisulfite and sodium metabisulfite give a better straightening effect than compositions comprising sodium metabisulfite alone.

Sodium Sulfate

When added to a composition according to the present invention, sodium sulfate ($Na_2SO_4$) drives the dynamic equilibrium toward the formation of sodium metabisulfite and away from the formation of sodium bisulfite (which led to the release of sodium dioxide).

Additionally, sodium sulfate is able to boost the activity of TGase. Therefore, compositions comprising sodium bisulfate and TGase give a better straightening effect than compositions comprising the same amount of TGase alone.

We stress that in a composition according to embodiments of the present invention, the sodium metabisulfite and the sodium bisulfite are in dynamic equilibrium. That is, in the composition, sodium metabisulfite is being transformed into sodium sulfite, and vice versa, but the ratio of sodium metabisulfite to sodium bisulfite has stabilized, having very little fluctuation over a significant period of time. A "significant period of time" is defined in the next paragraph in regard to pH drift.

A composition in which sodium metabisulfite and sodium bisulfite are present, but not in dynamic equilibrium, does not anticipate compositions described herein. If, for example, both materials were present in a prior art composition, but some how were prevented from reacting with each other, or some how the reaction had stopped, then that composition does not meet a claim to a composition in which the sodium metabisulfite and sodium bisulfite are in dynamic equilibrium.

The added sodium sulfate acts as an ionic buffer, maintaining the pH of the product within a desired range for a significant period of time; for example about 5.0 to about 7.5, more preferably about 5.5 to about 7.0, even more preferably, about 6.0 to about 6.5, and most preferably, 6.0 to 6.2; or for example, the defined range of pH might be 5.0-6.5, more preferably 5.5-6.0. Preferably, in a sealed container at ambient atmospheric conditions, the pH of a commercial composition according to one or more embodiments of the present invention is stabilized in a defined range for at least thirty days, more preferably at least sixty days, more preferably at least ninety days, more preferably at least one-hundred and eighty days, more preferably at least one year, and most preferably at least two years. Also, preferably, in a sealed container stored at 50° C., the pH of a commercial composition according to one or more embodiments of the present invention is stabilized in a defined range for at least seven days, more preferably at fourteen days, more preferably at least thirty days, and most preferably at sixty days.

Furthermore, due to the enhanced activity of TGase provided by sodium sulfate, and the reducing power of sodium sulfite, it may be possible to lower the concentration of TGase, to achieve a comparable activity. This is an unexpected advantage over the compositions of parent application U.S. Ser. No. 13/013,482, considering the relative expense and fragility of TGase.

The amount of sodium sulfite and sodium sulfate that should be added to a composition of the present invention is called out as a ratio of total sulfites to total sulfates. For example, the ratio of sulfites to sulfates may be any ratio between 1:1 and 10:1. For example, the ratio may be, 1.5:1, 2:1, 2.5:1, 3:1, 3.5:1, 4:1, 4.5:1, 5:1, and so on. All ratios between 1:1 and 5:1 are explicitly disclosed herein, and any two of those ratios may serve as inclusive endpoints for a range explicitly disclosed herein. For example, a composition according to the present invention may comprise: 6.7% sodium metabisulfite, 3% sodium sulfite and 2% sodium sulfate. In this case, the ratio of sulfites to sulfates is 4.85:1. In another example, a composition according to the present invention may comprise: 3.0% sodium metabisulfite, 1.5% sodium sulfite and 1% sodium sulfate. In this case, the ratio of sulfites to sulfates is 4.5:1.

In compositions according to the present invention, and in methods of making such compositions, it is preferable if the sodium sulfate ($Na_2SO_4$) is added to the composition before the sodium metabisulfite. By adding sodium sulfate to the composition before sodium metabisulfite, we increase the equilibrium concentration of sodium sulfate (the end product), which ultimately stabilizes the concentration of sodium metabisulfite (the initial product). Furthermore, by adding the adding sodium sulfate to the composition before sodium metabisulfite, we can stabilize the pH of the composition at a value above about 5, which will significantly reduce the amount of sodium dioxide released from sodium sulfate.

Preferably, compositions of the present invention do not use hydroxide compounds, such as sodium hydroxide, as pH adjusters.

Preferably, compositions according to the present invention are aqueous. We expect the ionic buffer/oxygen scavenging system to work less well in anhydrous compositions or compositions with relatively little water. Preferably, compositions of the present invention comprise at least 20% water, more preferably at least 30%, more preferably at least 40%, more preferably at least 50%, more preferably at least 60%, and most preferably at least 70% water.

Other Considerations of the Composition and Its Use

Heat and/or surfactants may degrade the activity of transglutaminase. For example, the stability of transglutaminase is compromised if it is heated in excess of 35-40° C. Thus, care should be taken in handling, storage, processing, manufacture, and distribution to ensure that the TGase is not exposed to temperatures of 35° C. or greater, for a period of time that would increase the temperature of the TGase above 35° C.

Furthermore, we have observed that after application to the hair, a composition according to the present invention should be allowed to dwell on the hair for about 15 to about 45 minutes. A preferred time to dwell is between 25 and 45 minutes, particularly about 30 minutes. The dwell time for effective straightening is dramatically less than a typical known commercial straightening product, which requires 48-72 hours of dwell time, before the user can wash it out. This is a very significant advantage of the present invention.

Furthermore, anionic surfactants, especially anionic surfactants in the presence of heat in excess of 35° C. can degrade the activity of TGase. Thus, care should be taken in formulation to select surfactants that will not significantly alter the activity of the transglutaminase under the intended conditions of use. If the nature of the composition is such that TGase and anionic surfactant would be sequestered from each other, then it may be possible to include anionic surfactant in compositions according to the present invention without harming the TGase. Otherwise, it is preferable if anionic surfactant is not used in the composition. Examples of anionic surfactants include: sulfates, sulfonates, phosphates and carboxylates. Sulfates include alkyl sulfates, such as ammonium lauryl sulfate and sodium lauryl sulfate (a.k.a. sodium dodecyl sulfate); alkyl ether sulfates, such as sodium laureth sulfate (a.k.a. sodium lauryl ether sulfate (SLES)), and sodium myreth sulfate. Sulfonates include docusates, such as dioctyl sodium sulfosuccinate; sulfonates fluorosurfactants, such as perfluorooctanesulfonate (PFOS), and perfluorobutanesulfonate; and alkyl benzene sulfonates. Phosphates include alkyl aryl ether phosphate and alkyl ether phosphate. Carboxylates include alkyl carboxylates, such as fatty acid salts (soaps) and sodium stearate; sodium lauroyl sarcosinate; carboxylate fluorosurfactants, such as perfluorononanoate and perfluorooctanoate.

Compositions of the present invention must also satisfy additional criteria. For example, the compositions must be cosmetically acceptable and commercially viable. "Cosmetically acceptable" and commercially viable" or the like, usually imply that a composition is safe to the consumer and stable under typical conditions of manufacture, distribution and consumer use. By "stable", we mean that one or more characteristics of a personal care composition do not deteriorate to an unacceptable level within some minimum period of time after manufacture. Preferably, that minimum time is six months from manufacture, more preferably one year from manufacture, and most preferably more than two years from manufacture. "Safe" implies, among other things, that a composition satisfies all legal regulations related to products applied topically to the hair of the head.

Compositions of the present invention must be efficacious when used in reasonable amounts. A composition is considered effective to permanently straighten human hair, only if the amount of composition applied to the hair is what a consumer or salon professional would consider reasonable. For example, if a lotion composition reshapes the hair, but a gallon of the composition is required, then this is not an effective composition according to the present invention. A person skilled in the art of personal care hair products has a very good idea of what consumers and salon professionals would consider reasonable. The amount of a composition of the present invention required for one treatment depends on the type and amount of hair being treated and on the desired effect. However, experience suggests that about 200 grams of a composition according to the present invention, applied to the hair, is sufficient and effective to complete a treatment of a full head of shoulder length hair. This number is provided only for guidance, and more or less may be used as needed.

Furthermore, when tourmaline is used, the base composition should not absorb too much of the radiation emitted by the tourmaline, and the base composition should not interfere with activation or deactivation of the tourmaline.

Given these guidelines, compositions according to the embodiments disclosed herein, may be readily formulated into a variety of product types that are suitable for topical delivery to the hair. The composition may be a mixture, a suspension, an emulsion (water/oil, oil/water, water/silicone, silicone/water), a liquid, an aerosol, a gel, a cream, a lotion, a serum, or mousse, just to name a few. The composition may be in the form of a styling product, a coloring product, a conditioner or a shampoo, for example. Methods and guidelines for formulation can be found, for example, in Harry's Cosmeticology, 8th edition, M. Reiger, Ed. 2000, the contents of which are incorporated herein by reference.

Some preferred embodiments of the present invention are silicone-in-water emulsions or suspensions, relatively thin, to allow dispersion of active sulfites and sulfates throughout the composition, especially particulate materials. A thinner emulsion or suspension also increases penetration and absorption of actives at the delivery site. In these embodiments, active particulates may be dispersed within or without the emulsion droplets. As a guide, some embodiments of the present invention may have a viscosity of 1,000-30,000 cps; more preferably 1,000-20,000 cps; even more preferably 2,000-10,000 cps; and most preferably 4,000-7,000 cps (LVT, #3, 12 RPM, 1 minute, factor=100). From this, a person of skill in the art may determine equivalent viscosity readings if using a different spindle and speed. Preferred embodiments of the invention, will comprises active sulfite particles ranging from about 0.5-5 microns, dispersed in emulsion droplets that range from about 10-100 microns.

Within the guidelines discussed, a composition according to the present invention may contain any ingredients that are known to provide a benefit to the hair, any ingredients required to render a stable product, and any ingredients that render the product more cosmetically acceptable or commercially viable. For example, compositions according to the present invention may advantageously contain hair coloring agents. Hair coloring reactions of the type well known in the art, and disulfide bond cleavage as described herein, may exhibit synergistic effects.

Preferably, compositions of the present invention comprise no hydroxide compounds, no thiols, no cysteine compounds, and no formaldehyde compounds. In parent application U.S. Ser. No. 13/013,482, data was presented to show that the compositions disclosed therein, cause less than half the damage of several commercially available products. The improvements that we describe herein do not change that. Compositions of the present invention are similarly expected to inflict significantly less damage on human hair than commercially available products whose principal hair straightening agent is cysteine, formaldehyde, sodium hydroxide, or thiols.

To the extent that one or more undesirable odors may be given off by the composition, these may be masked with one or more natural or synthetic fragrances or maskants. The following are examples of some embodiments of compositions according to the present invention.

TABLE 1

| Phase | Ingredient | Percent by weight of Composition | | | | |
|---|---|---|---|---|---|---|
| | | Example 1 | Example 2 | Example 3 | Example 4 | Example 5 |
| 1 | Deionized water | 41.85 | 50.35 | 56.55 | 42.25 | 41.05 |
| | Hydroxyethylcellulose | 0.50 | 0.60 | 0.60 | 0.50 | 0.50 |
| 2 | Tetrasodium EDTA | 0.10 | 0.10 | 0.10 | 0.10 | 0.10 |
| 3 | Hexylene glycol | 2.00 | 2.00 | 2.00 | 2.00 | 2.00 |
| | Glycerine | 1.00 | 1.00 | 1.00 | — | 1.00 |
| | Xanthan gum | 0.35 | 0.25 | 0.25 | 0.35 | 0.35 |
| 4 | Deionized water | 5.00 | 5.00 | 5.00 | 5.00 | 5.00 |
| | Sodium sulfate | 2.00 | 2.00 | 1.00 | 2.00 | 2.00 |
| 5 | Deionized water | 20.00 | 20.00 | 20.00 | 20.00 | 20.00 |
| | Red tourmaline | 1.00 | 1.00 | 1.00 | 1.00 | 1.00 |
| | Sodium metabisulfite | 7.70 | 6.70 | 3.00 | 7.75 | 6.70 |
| | ActivaTG-TI[1] | 2.00 | 2.00 | 2.00 | 2.00 | 2.00 |
| | Sodium sulfite | 2.00 | 3.00 | 1.50 | 2.00 | 3.00 |
| | Polylysine (25% aq. sol.) | 0.0001 | 0.0001 | 0.0001 | 0.0001 | 0.80 |
| 6 | Jeecide CAP-5[2] | 1.00 | 1.00 | 1.00 | 1.00 | 1.00 |
| | PEG/PPG-18/18 Dimethicone | 2.50 | 1.00 | 1.00 | 3.00 | 2.50 |
| | Methyl trimethicone | 1.00 | 1.00 | 1.00 | 1.50 | 1.00 |
| | KSG-210[3] | 5.00 | — | — | 5.50 | 5.00 |
| | Cetyl PEG/PPG-10/Dimethicone | 3.00 | 1.00 | 1.00 | 3.00 | 3.00 |
| | Gransil MMT fluid[4] | 0.0001 | 0.0001 | 0.0001 | 0.0001 | 0.0001 |
| | Gransil PMT fluid[5] | 0.0001 | 0.0001 | 0.0001 | 0.0001 | 0.0001 |
| | Dimethicone/dimethiconol | — | — | — | 0.50 | — |
| | Propanediol | — | — | — | 0.50 | — |
| | Fragrance | q.s. | q.s. | q.s. | q.s. | q.s. |

[1] Transglutaminase/maltodextrose
[2] Phenoxyethanol/caprylyl glycol/potassium sorbate/water/hexylene glycol
[3] Dimethicone/Dimethicone/PEG-10/15 crosspolymer
[4] Dimethicone/mercaptopropyl methicone copolymer
[5] Dimethicone/mercaptopropyl methicone copolymer/phenyl trimethicone Table 2 shows pH values verses time for the two formulae shown as Examples 4 and 5, in the table 1 above. Four test samples were prepared, two according to Example 4 and two according to Example 5. One of each was stored at RT and one of each was stored at 50° C.

TABLE 2

| | Sample | | | |
|---|---|---|---|---|
| Days after manufacture | Example 6 Formula of Example 4 at RT | Example 7 Formula of Example 4 at 50° C. | Example 8 Formula of Example 5 at RT | Example 9 Formula of Example 5 at 50° C. |
| 1 | 5.80 | 5.80 | 5.72 | 5.72 |
| 2 | | 5.69 | | 5.61 |
| 4 | 5.84 | 5.86 | | |
| 5 | 5.93 | 5.82 | | |
| 6 | 5.98 | 5.82 | | |
| 7 | 5.91 | 5.75 | 5.42 | 5.46 |
| 8 | 5.99 | 5.91 | | |
| 11 | 5.84 | 5.75 | | |
| 12 | | | 5.99 | 5.91 |
| 13 | | | 5.84 | 5.96 |
| 14 | | | 5.86 | 5.86 |
| 15 | | | 5.90 | 5.92 |
| 19 | | | 5.92 | 5.95 |
| 20 | | | 5.94 | 5.96 |
| 21 | | | 5.90 | 5.85 |
| 22 | | | 5.99 | 6.02 |
| 25 | | | 5.87 | 5.89 |

Results:

After 7 days at RT, the pH of the formula of Example 4 remained within 5.80-5.99, while for the 50° C. sample, the pH remained within 5.75-5.91. After 25 days at RT, the pH of the formula of Example 5 remained within 5.42-5.99, while for the 50° C. sample, the pH remained within 5.46-6.02. In all cases, the trendline is nearly flat, slightly increasing. We may conclude the buffer system herein described is effective. The dynamic equilibrium between sodium metabisulfite and sodium bisulfite is preserved in favor of sodium metabisulfite, and the efficacy of the compositions is preserved.

Method of Making

Any of the above formulae may be prepared according to the following procedure.

Step 1: prepare a composition according to the following phases:

Phase
1. Add the water to the main kettle; at RT slowly add the hydroxyethylcellulose under propeller mixing. Allow to hydrate for at least 30 minutes, increasing the propeller if needed.
2. Add tetrasodium EDTA to the main kettle, and mix until clear, uniform and lump free.
3. Separately mix hexylene glycol, glycerine and Xanthan gum. Mix well until blended, then add to the main kettle.
4. Separately combine water and sodium sulfate under propeller mixing until all solid is dissolved. This phase may be heated slightly to help the solid dissolve. Once all of the solid is dissolved, add to the main kettle.
5. Using a propeller at RT, separately mix water, tourmaline, sodium metabisulfite, transglutaminase, sodium sulfite and polylysine, until all particles are dissolved. Once all of the particles are dissolved, add to the main kettle.
6. Separately mix silicone/oil phase, and add to the main kettle. Mix until uniform.

Step 2: Confirm that pH is within a predetermined range; for example, 5.0-7.5, more preferably about 5.5 to about 7.0, even more preferably, about 6.0 to about 6.5, and most preferably, 6.0 to 6.2.

Step 3: Confirm that viscosity is within a predetermined range; for example, 1,000-30,000 cps; more preferably 1,000-20,000 cps; even more preferably 2,000-10,000 cps; and most preferably 4,000-7,000 cps (LVT, #3, 12 rpm for 1 minute, factor=100).

Step 3 may be performed before step 2.

Methods of Use

Compositions according to the present invention may be used to straighten non-straight hair, either a whole head of hair or any portion thereof. The present invention includes the use of a composition as disclosed herein to straighten non-straightened hair.

We describe a preferred method of using a composition according to the present invention. As an optional first step, the hair should be washed with a clarifying shampoo to strip the hair of any surface contamination or anything that might interfere with the actives on the composition. If shampooing is not used, the hair may be wetted before applying the composition. Preferably, the hair is wet when the composition is applied.

Thereafter, a portion of non-straightened hair is treated by applying a composition according to the present invention to the non-straightened hair. The composition may or may not be agitated (i.e. shaken) prior to use, as directed by instructions included with a commercial product version of the composition. Enough product is applied to thoroughly coat the hair from root to tip Preferably, the hair being treated is coated from the roots to the ends. For example, at least 50% of the hair, from the root to the end is coated with the composition, more preferably at least 75%, most preferably at least 95%. As noted above, for an average head of woman's hair, this may require 200 gm of composition, more or less depending on the actual amount of hair that is being treated.

After the composition is applied to the hair, the composition should be allowed to dwell on the hair for a minimum dwell time, before further treatment. For example, it is preferable if the dwell time is at least 10-20 minutes, more preferably at least 20-30 minutes, even more preferably at least 35 minutes, and most preferably 30-35 minutes. During the dwell time, it is especially important that the composition on the treated hair is not exposed to temperatures in excess of 45° C., preferably not in excess of about 40° C., and more preferably not in excess of about 35° C. During the dwell time, S—S bonds in the hair structure are being reduced to Bunte salts by the sodium metabisulfite and sodium sulfite in the composition.

After the dwell time, as an optional, but preferred step, the hair should be thoroughly rinsed with water, preferably water at a temperature above ambient temperature. This will begin the process of oxidizing the Bunte salts back to S—S bonds, making the treatment permanent, as well as removing residue of the composition from the hair. To rinse the hair, the hair may be submerged in standing water or treated with running water. For example, a thorough rinse might be at least 5 minutes under running water.

After rinsing (or after the dwell time if rinsing was not done) the treated hair is set into a straightened configuration, by mechanical means. For example, the hair may be combed straight. If the hair is wet, a heating dryer may be used during of after setting the hair into a straightened configuration, to dry the hair. Excessive pulling of the hair is not necessary and should be avoided. Preferably, as a result of heated drying, the hair achieves a temperature of at least 50° C., more preferably at least 60°, and most preferably at least 70° C., to dry the hair and to activate the tourmaline, some of which will remain on the hair, even if the optional step of rinsing is used. Examples of heated dryers include hot air blowers, radiant heating, and hot irons). Alternatively, a heating dryer or other heating means may be used to activate the tourmaline any time after the composition is applied to the non-straightened hair.

Optionally, at any point after the step of allowing the composition to dwell on the hair, a hot iron may be applied to the treated hair in the usual manner of hot irons. The hot iron is optional and may be used to provide shine, as well as to activate the tourmaline. It is not needed for straightening, and cannot effect permanent straightening. If a hot iron is used, then preferably the step of rinsing the hair after the dwell time is included. This will eliminate or significantly reduce any smoking that a hot iron would otherwise cause. That there is little or no smoking is a significant health advantage of methods according to the present invention. Also, if a hot iron is used, then preferably the hot iron is passed through the treated hair at least twice, more preferably at least 5 times and most preferably up to 10 times. Preferably the hot iron is at least 350° F., more preferably at least 400° F., and most preferably about 450° F.

Oxidizing of Bunte salts will continue for some time (i.e. days), each time the hair is wet with water. The oxidation of Bunte salts may be enhanced by shampooing with an alkaline product, such as a shampoo having a pH between 7.0 and 9.0.

What is claimed is:

1. A topical composition comprising:
a cosmetically acceptable aqueous base;
transglutaminase;
sodium metabisulfite ($Na_2S_2O_5$) in dynamic equilibrium with sodium bisulfite ($NaHSO_3$), and
a system that drives the equilibrium toward the formation of sodium metabisulfite, and away from the formation of sodium bisulfite, and that reduces S—S bonds in hair;
the topical composition for straightening the hair having a pH from about 5.0 to about 7.5 wherein the system is a pH buffer/oxygen scavenging system comprising sodium sulfate ($Na2SO4$), and sodium sulfite ($Na_2SO_3$), that is able to maintain the pH of the composition between about 5.0 and about 7.5, for at least thirty days and wherein the ratio of sodium sulfite ($Na_2SO_3$) to sodium sulfate ($Na_2SO_4$) is between 1:1 and 10:1 and the topical composition further comprising about 0.00001% to about 2% of polylysine and the topical composition having no sodium hydroxide, no potassium hydroxide, no lithium hydroxide, no guanidine hydroxide, no thioglycolates, no cysteine, no ammonium sulfite, no ammonium bisulfite, or formaldehyde, wherein the topical composition is for straightening the hair.

2. A topical composition of claim 1 wherein the pH buffer/oxygen scavenging system is able to maintain the pH of the topical composition for straightening the hair between about 6.0 and about 6.5, for at least thirty days.

3. A topical composition for straightening the hair according to claim 1 wherein the transglutaminase is calcium independent, and present in an amount that provides at least 0.5 Units of activity per gram of topical composition for straightening the hair.

4. A topical composition for straightening the hair according to claim 1 wherein the transglutaminase is calcium dependent, present in an amount that provides at least 0.5 Units of activity per gram of topical composition for straightening the hair, and the topical composition for straightening the hair further comprises calcium.

5. A topical composition for straightening the hair according to claim 1 further comprising tourmaline.

6. A method of straightening hair comprising the steps of:
treating non-straightened hair by applying a topical composition for straightening the hair according to claim 1;
allowing the topical composition for straightening the hair to dwell on the treated hair for at least 10 minutes, while not being exposed to temperatures in excess of 45° C., such that S—S bonds in the hair are reduced by the topical composition for straightening the hair;
setting the treated hair into a straightened configuration.

7. A method according to claim 6 wherein:
after the step of allowing the topical composition for straightening the hair to dwell, the treated hair is wetted; and
during or after the step of setting the hair, a heated dryer is used to dry the treated hair.

8. A method according to claim 6 wherein:
after the step of allowing the topical composition for straightening the hair to dwell, a hot iron having a temperature of at least 350° F., is passed through the treated hair, at least twice.

9. A method according to claim 6 wherein:
after the step of applying a topical composition for straightening the hair to non-straightened hair, the tourmaline is activated.

10. A method of claim 6 wherein:
before the step of applying a topical composition for straightening the hair to non-straightened hair, the non-straightened hair is wetted.

11. The method of claim 6 wherein after the step of setting the treated hair, the hair is shampooed.

* * * * *